United States Patent [19]

Zubovics et al.

[11] Patent Number: 5,235,097
[45] Date of Patent: Aug. 10, 1993

[54] PROCESS FOR THE PREPARATION OF 2,2-DIMETHYL-5-(2,5-DIMETHYL-PHENOXY)-PENTANOIC ACID, INTERMEDIATES FOR PREPARING THIS COMPOUND AND PROCESS FOR PREPARING THE INTERMEDIATES

[75] Inventors: Zoltán Zubovics; Gábor Fehér; Lajos Toldi; Gábor Kovács; Antal Simay; Éva Kovács nee Bozó; Imre Moravcsik; Ferenc Szederkényi; György Krasznai; Györgyi Vereczkey nee Donáth; Kálmán Nagy, all of Budapest, Hungary

[73] Assignee: EGIS Gyogyszergyar, Hungary

[21] Appl. No.: 890,781

[22] Filed: Jun. 1, 1992

Related U.S. Application Data

[62] Division of Ser. No. 698,081, May 10, 1991, Pat. No. 5,155,260.

[30] Foreign Application Priority Data

May 11, 1990 [HU] Hungary .............................. 2997/90

[51] Int. Cl.$^5$ .............................................. C07C 69/63
[52] U.S. Cl. ..................................... 560/230; 544/399
[58] Field of Search ......................... 560/230; 544/399

[56] References Cited

U.S. PATENT DOCUMENTS

| | | | |
|---|---|---|---|
| 3,674,836 | 7/1972 | Creger | 562/471 |
| 3,759,986 | 9/1973 | Creger et al. | 562/471 |
| 3,847,994 | 11/1974 | Creger et al. | 562/471 |
| 4,665,226 | 5/1987 | Kearney | 562/471 |

*Primary Examiner*—Paul J. Killos
*Attorney, Agent, or Firm*—Beveridge, DeGrandi, Weilacher & Young

[57] ABSTRACT

The invention relates to an improved process for the preparation of 2,2-dimethyl-5-(2,5-dimethylphenoxy)-pentanoic acid of Formula (I)

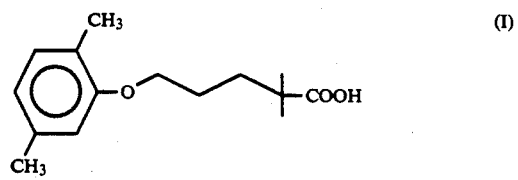

which comprises reacting an ester of the general Formula (X)

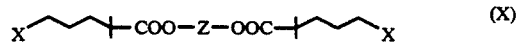

wherein X represents halogen and Z stands for a straight or branched chain $C_{1-8}$ alkylene group optionally substituted by one or two 2,2-dimethyl-5-halopentanoyloxy group(s), wherein halo represents chlorine or bromine, and in which alkylene group one or two methylene group(s) may be optionally replaced either by hetero atom(s) or by a bivalent heterocyclic group—with an alkali salt of 2,5-dimethylphenol of Formula (II)

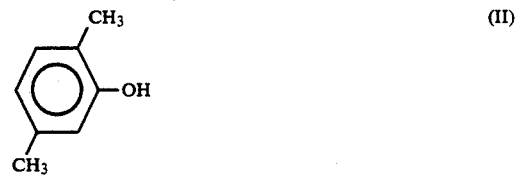

or with an ester of the latter formed with a lower alkanoic acid, and hydrolizing the aryloxy-substituted ester of the general Formula (XI) thus obtained.

(Abstract continued on next page.)

ABSTRACT
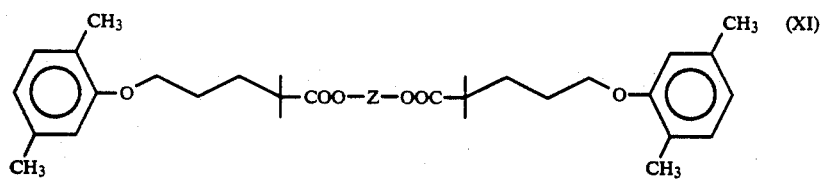
Furthermore the invention relates to intermediate compounds of the general Formula (X), wherein X and Z are as stated above, and to a process for the preparation thereof.
8 Claims, No Drawings

PROCESS FOR THE PREPARATION OF 2,2-DIMETHYL-5-(2,5-DIMETHYL-PHENOXY)-PENTANOIC ACID, INTERMEDIATES FOR PREPARING THIS COMPOUND AND PROCESS FOR PREPARING THE INTERMEDIATES

This is a division of application Ser. No. 07/698,081, filed May 10, 1991, now U.S. Pat. No. 5,155,260.

The present invention relates to a new and improved process for the preparation of 2,2-dimethyl-5-(2,5-dimethylphenoxy)-pentanoic acid (Gemfibrozil, Lopid) of formula (I),

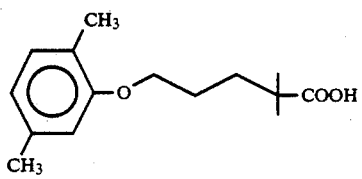

to new intermediates useful in the preparation thereof, further to a process for the preparation of said intermediates.

It is known that several aryloxyalkanoic acids, especially 2,2-dimethyl-5-(2,5-dimethylphenoxy)-pentanoic acid can be used to regulate blood lipid levels, so they are valuable pharmaceutical agents (U.S. Pat. No. 3,674,836 and the so-called Helsinki study of M. H. Frick et al.: The New England Journal of Medicine, 317, 1237 [1987]).

The known synthesis methods for the preparation of Gemfibrozil can be classified into two groups, depending on the sequence of the reaction steps attaching the three main structural elements of the molecule, namely the part derived from the phenol, the 1,3-propylene chain and the part derived from isobutyric acid.

The two different synthesis routes are illustrated by the attached reaction scheme.

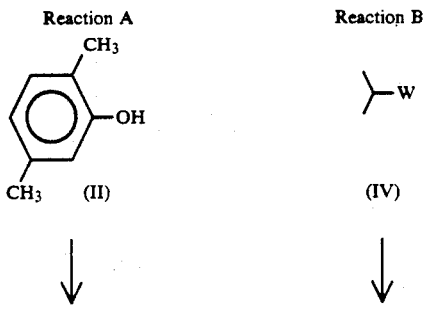

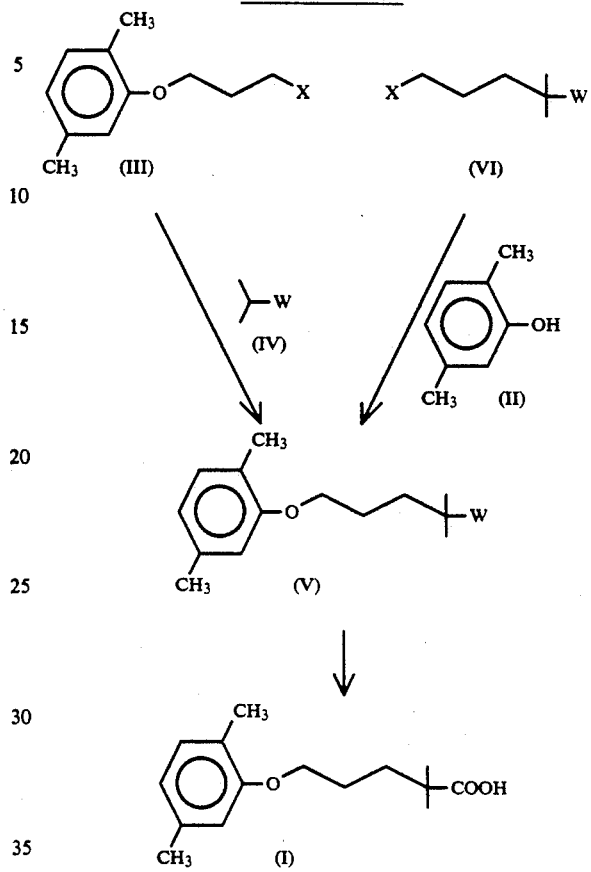

According to Route A in this scheme 2,5-dimethylphenol of the Formula (II) and a $C_3$ alkylene chain are coupled first, then the substituted ether of the general Formula (III) thus obtained, wherein X represents a leaving group such as halogen atom or sulfonyloxy group, is reacted with isobutyric acid or with a derivative of the general Formula (IV) thereof, wherein W represents carboxy or a group which can be converted into carboxy as detailed below. The compound of the general Formula (V) thus obtained, wherein W is as stated above, is then converted to the desired compound of the Formula (I) by known methods chosen according to the nature of W.

On the other hand, according to Route B in the scheme, the alkylene chain is attached first to isobutyric acid or to a derivative or analogue thereof of the general Formula (IV), then the intermediate of the general Formula (VI) thus obtained, wherein X and W are as stated above, is reacted with 2,5-dimethylphenol of the Formula (II), and the compound of the general Formula (V) thus obtained, wherein W is as stated above, is converted into the desired compound of the formula (I).

The known syntheses providing Gemfibrozil of the Formula (I) are summarized according to the above-specified classification as follows:

Route A

The German patent specification No. 1,925,423 (or the corresponding U.S. Pat. No. 3,674,836), which was the first to disclose the desired compound, teaches the preparation thereof by reacting 2,5-dimethylphenol with sodium hydride in an aprotic solvent, reacting the sodium salt thus obtained with a 1,3-dihaloalkane, and reacting the haloalkyl-aryl ether of the general Formula (III) thus obtained, wherein X represents halogen, in tetrahydrofuran with an alpha-carbanion formed from a compound of the general Formula (IV), wherein W stands for carboxy or alkoxycarbonyl, obtained from isobutyric acid or an ester thereof. The alpha-carbanion is prepared with lithium diisopropylamide, while in case of the isobutyric acid the carboxylate salt is formed either with the same base or with sodium hydride or magnesium oxide. The yields of these reactions are not published in the specification, but according to estimations based on analogies detailed in U.S. Pat. No. 4,665,226 the process described in U.S. Pat. No. 3,674,836 provides the desired compound of the Formula (I) in a total yield of only about 39 to 46%, based on the starting phenol of the Formula (II).

According to our investigations the drawback of this method, in addition to the low yield, resides in the fact that the conversion of the second reaction step is low (about 40%), and the recovered unreacted intermediate of the general Formula (III) requires purification before recycling.

According to another method described in Spanish patent specification No. 534,473 an intermediate of the general Formula (III), wherein X represents mesyl group, is used, and the final step carried out with isobutyric acid is performed in dimethyl sulfoxide, in the presence of sodium hydride, at a temperature of 50° C. The yield of this step is 76%, while that of the production of the mesyloxy compound is not published. As the dimethyl sulfoxide-sodium hydride system may be explosive at temperatures between 50° C. and 60° C. (Houben-Weyl: Die Methoden der organischen Chemie, Vol. 5/2a, p. 360), this method can not be recommended for industrial-scale manufacture.

If, instead of the isobutyric acid or a derivative thereof, that is a compound bearing two methyl groups in alpha position, an analogous derivative bearing only one methyl group in alpha position (e.g. a methyl malonic acid diester) is alkylated with the haloalkyl ether of the general Formula (III), the reaction can be carried out with a base that can be handled easier, e.g. with sodium ethoxide in ethanol (Spanish patent specification No. 549,469). In this way an analogous derivative of the compound of the Formula (I) bearing one methyl group less on the alpha carbon atom is produced. Even in this case, however, lithium diisopropylamide has to be used in the final reaction step to introduce the methyl group. The yield of the final product formed according to this method is 70%, based on the haloalkyl ether of the general Formula (III), but according to the known methods serving for the preparation of said haloalkyl ethers (e.g. U.S. Pat. No. 3,674,836; J. Augstein et al.: J. Med. Chem. 8, 356 [1965]) these can be produced only in yields of about 30%. Thus the total yield of this synthesis is low, it does not exceed 21%, based on the starting phenol of the Formula (II).

According to a further variant of Route A a Grignard reagent is prepared from the haloalkyl ether of the general Formula (III), wherein X stands for bromine, which is then reacted with acetone. The carbinol of the general Formula (V) thus obtained, wherein W represents hydroxy, is reacted with thionyl chloride to produce the analogous derivative containing chlorine as W. Then, after formation of another Grignard reagent and reaction of the latter with carbon dioxide, the desired compound of Formula (I) is obtained (Spanish patent specification No. 549,470). The total yield of this method calculated upon the haloalkyl ether of the general Formula (III) is 65% but, owing to the low yield of the haloalkyl ether formation mentioned in the previous paragraph, the total yield of the compound of Formula (I) calculated upon the starting 2,5-dimethylphenol is only 20%.

According to further analogous synthesis variants an aldehyde of the general Formula (IV), wherein W represents formyl or the corresponding Schiff base (wherein W stands for a group of the Formula —CH=N—alkyl), or a nitrile of the general Formula (IV), wherein W represents cyano, instead of the isobutyric acid or the appropriate derivative thereof, is alkylated with a haloalkyl ether of the general Formula (III). The intermediate of the general Formula (V) thus obtained is then converted into the compound of Formula (I) by methods known per se (U.S. Pat. No. 3,759,986 and 3,847,994). The yields of these reactions are not given but, considering the number of the reaction steps necessary to prepare both the starting substances and the final product itself, it may be supposed that this method is less economical.

According to a further process for the preparation of Gemfibrozil an aldehyde of the general Formula (V), wherein W denotes formyl group, which can be produced e.g. as described in the previous paragraph, is oxidized with the oxygen of the air, in the presence of a noble metal catalyst, into the desired carboxylic acid. The yield of the oxidation is about 70%, but that of the preparation of the aldehyde of the general Formula (V) is not known (U.S. Pat. No. 4,126,637).

As for industrial-scale realization all of the synthesis variants belonging to Route A shown in the attached reaction scheme have a serious drawback, namely that the haloalkyl ether of the general Formula (III) (wherein X is bromine) used as intermediate can be prepared only in a low yield of about 30 to 40%, whereby the total yield of the compound of Formula (I) based on the relatively expensive starting 2,5-dimethylphenol is rather low, consequently these methods are not economical.

Route B

The starting substance of the known processes is not the free isobutyric acid but an appropriate derivative thereof, to which at first the $C_3$ alkylene chain is attached followed by coupling with the phenol. Thus, according to the method described in Spanish patent specification No. 517,665, an aryloxyalkyl ketone of the general Formula (IV), wherein W represents benzoyl, is cleaved with potassium tert-butylate, in the presence of anisole to afford the desired acid of Formula (I). The yield of the synthesis is not published in the specification.

Considering the yields, U.S. Pat. No. 4,665,226 seems to provide the most advantageous method. According to this process a lower alkyl ester of isobutyric acid, preferably the isobutyl ester thereof [a compound of general Formula (IV), wherein W represents isobutoxycarbonyl] is alkylated with 1-bromo-3-chloropropane in tetrahydrofuran, in the presence of lithium diisopropylamide, with 94% yield. The halogenated ester of the general Formula (VI) thus obtained, wherein X stands for chlorine and W represents isobutoxycarbonyl, is then reacted with the anhydrous sodium salt of 2,5-dimethylphenol of Formula (II) in a mixture of toluene and dimethyl sulfoxide, in the presence of sodium iodide as catalyst, and the ester of Gemfibrozil thus obtained [a compound of the general Formula (V), wherein W is as stated above] is subjected to hydrolysis with an excess of a base, without isolation, directly in the reaction mixture in which it was formed. The solvent is then distilled off, the crude Gemfibrozil salt is purified by extraction of its alkaline aqueous solution with hexane and the final product is isolated after a subsequent acidification. According to the specification the total yield in the two last reaction steps, namely the coupling with 2,5-dimethylphenol and the hydrolysis, amounts to 92%. So the desired compound of Formula (I) is obtained in an excellent yield of 86%, based on the starting isobutyl isobutyrate.

According to our investigations both the alkylation of the isobutyrate and the coupling with phenol, furthermore the hydrolysis can really be carried out with high yields, comparable to those given in the above-referred specification. So this method would seem to be the most favourable one among the known processes, but according to our experiences it has severe drawbacks, too. The most serious disadvantage of it resides in the fact that the quality of the Gemfibrozil prepared by this method does not comply with the requirements specified in U.S. Pharmacopoeia, and even the recrystallization mentioned in the specification does not afford the compound of Formula (I) in such a high purity. According to our investigations the final purification of the active substance providing the desired compound in a quality required by the U.S. Pharmacopoeia, to which the specification in question does not provide any solution, can be carried out with a loss of about 15 to 18%. Another disadvantage of this method is that the purification and drying of the lower alkyl esters of isobutyric acid used as starting substances are rather complicated. Namely, it is known that many low alkyl esters of isobutyric acid, e.g. the isobutyl ester thereof, form an azeotrope with several solvents, so they can not be separated from these solvents by a simple distillation (Beilstein: Handbuch der organischen Chemie, Vol. 2, suppl. III, pp. 643-647). Should this ester be prepared by any of the known methods, e.g. by esterifying isobutyric acid, oxidizing isobutanol or subjecting isobutyraldehyde to Tishtchenko reaction (Beilstein 2, H 291, I 128, II 260, III 647, IV 847), it has to be distilled off before use, and what is more, for the reasons mentioned above, via a column, which process leads to considerable losses and expenses. The above-mentioned ester has to be practically anhydrous, as the base (lithium diisopropylamide) used in the next reaction step for the C-alkylation, is decomposed by water. According to our investigations the ester can not be properly dried by azeotropic distillation or by drying over calcium chloride, but only by distillation over phosphorous pentoxide, and this latter method is cumbersome on industrial-scale and results in considerable losses, too. That is why the total yield of the pure Gemfibrozil produced by the above-described synthesis—calculated upon the starting isobutyric acid—is, according to our experiments, only about 45%.

So, taking into consideration what has been said above, a true evaluation of any method providing Gemfibrozil can only be obtained by comparing the productivity and economic points of the whole synthesis. Thus, e.g. in case of U.S. Pat. No. 4,665,226 all the three reaction steps, namely the esterification, the alkylation and the coupling with phenol, and not merely the latter two steps are to be considered.

The method for the preparation of the lactone of Formula (VII)

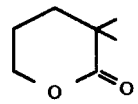

(VII)

according to published European patent application No. 219,177 can be considered as a special version of Route B. According to this method, first the allyl ester of isobutyric acid [a compound of the general Formula (IV), wherein W represents allyloxycarbonyl] is rearranged in toluene, in the presence of sodium hydride, into 2,2-dimethyl-4-pentenoic acid, which is then subjected to addition with hydrogen bromide to produce 5-bromo-2,2-dimethylpentanoic acid [a compound of the general Formula (VI), wherein X is bromine and W is a carboxy]. The latter compound is treated with an aqueous base to afford the lactone of Formula (VII) in excellent yield. Although it is mentioned in the specification that this compound can be used, among others, for the preparation of Gemfibrozil of Formula (I), neither the referred specification nor any other publication teaches how this process can be performed.

From the above facts it emerges that the hitherto known methods provide the desired compound of Formula (I) only in low yields and in qualities unsuitable for direct pharmaceutical use.

It is an object of the present invention to provide a process which overcomes the drawbacks of the known methods and enables the favourable preparation of the compound of Formula (I) with high yield and in a quality suitable for direct pharmaceutical use via intermediates which can be prepared and purified by simple methods.

It was found that the Gemfibrozil of Formula (I) can be prepared economically and by technologically simple methods by attaching isobutyric acid to an appropriate carrier, carrying out the necessary transformations specified below and finally splitting the desired compound off the carrier.

It is preferable to choose as carrier a molecule to which several (two, three or four) molecules of isobutyric acid can be attached. Thus, e.g. multivalent alcohols may serve as carrier, to which isobutyric acid can be attached by esterification. To the alpha carbon atoms of the isobutyryl (2-methylpropanoyl) groups of the multivalent esters thus obtained a gamma-halopropyl group can be attached by methods known per se. the halogen atom can be substituted by a 2,5-dimethylphenoxy group in a conventional manner, finally the Gemfibrozil molecule thus obtained can be split off the carrier by hydrolysis. It was found that the multivalent alcohols of the general Formula (VIII),

HO—Z—OH (VIII)

wherein Z stands for a straight or branched chain $C_{1-8}$ alkylene group optionally substituted by one or two hydroxy group(s), and in which alkylene group one or two methylene group(s) may be optionally replaced either by hetero atom(s), preferably oxygen and/or nitrogen atom(s), which latter may be optionally substituted by phenyl or $C_{1-4}$ alkyl optionally substituted by a hydroxy group, or by a bivalent heterocyclic group, such as piperazine-1,4-diyl group, can be used as carriers.

Preferred representatives of the alcohols of the general Formula (VIII) are e.g. the ethylene glycol, 1,2-propanediol, 1,3-propanediol, 1,4-butanediol, 1,6-hexanediol, 2-methyl-1,3-propanediol, 2,2-dimethyl-1,3-propanediol, 2-methyl-2-(n-propyl)-1,3-propanediol, 2-hydroxy-1,3-propanediol (glycerine), 2-hydroxymethyl-2-methyl-1,3-propanediol, 2,2-bis(hydroxymethyl)-1,3-propanediol (pentaerythrite), diethylene glycol, triethylene glycol, N-phenyl-diethanolamine, N-methyl-diethanolamine, triethanolamine, 1,4-bis(2-hydroxyethyl)-piperazine and the like.

Particularly preferred representatives of the multivalent alcohols of the general Formula (VIII) for the purpose of carrier are the following: 1,3-propanediol, 1,6-hexanediol, N-phenyl-diethanolamine and diethylene glycol.

When esterifying the multivalent alcohols of the general Formula (VIII) with isobutyric acid, the corresponding multivalent esters of the general Formula (IX) are obtained,

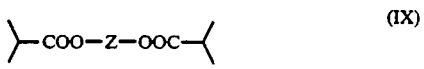
(IX)

wherein Z is as stated for the general Formula (VIII), except that if Z in this latter contains hydroxy group(s), then Z in the compound of the general Formula (IX) contains 2-methylpropanoyl group(s) at the corresponding site(s). So the multivalent esters of the general Formula (IX) contain, depending on the number of the hydroxy groups of the multivalent alcohols of the general Formula (VIII), at least two but optionally more (three or four) ester groups, that is 2-methylpropanoyloxy groups.

The multivalent esters of the general Formula (IX) are in part known compounds or can be prepared by methods known per se, e.g. by esterification of the multivalent alcohols of the general Formula (VIII) with isobutyric acid, using conventional methods.

A great advantage of the multivalent esters of the general Formula (IX) compared with the simple aliphatic esters used earlier for the preparation of Gemfibrozil resides in the fact that they do not form azeotropes either with water or with the usual organic solvents, so the solvents can readily be distilled off the solutions and the esters can be purified by simple distillation. Thus the esters of the general Formula (IX) can be obtained in anhydrous form with good yields and in the required purity. A further advantage of the multivalent esters is that even the crude products are sufficiently pure for use in the process according to the invention. So this method can easily be realized on industrial scale, too.

Furthermore, surprisingly it was found that the alpha carbon atoms of the acyl groups of the multivalent esters of the general Formula (IX) can be alkylated generally more readily and within a considerably shorter time than the simple aliphatic esters of the isobutyric acid used earlier for the preparation of Gemfibrozil. If said alkylation is performed with an 1,3-dihalopropane, the new halogenated multivalent esters of the general Formula (X) are obtained,

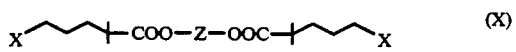
(X)

wherein X represents halo such as chlorine, bromine or iodine, and Z is as stated for the general Formula (VIII) except that if Z in the latter contains hydroxy group(s), then Z in the compound of the general Formula (X) contains 2,2-dimethyl-5-halopentanoyloxy group(s) at the corresponding site(s).

The compounds of the general Formula (X) may contain—depending on the number of the 2-methylpropanoyloxy groups of the starting esters of the general Formula (IX)—at least two, optionally three or four 2,2-dimethyl-5-halopentanoyloxy groups, and can be isolated and purified by methods known per se, but one may preferably use them for the next reaction step in crude form, without any purification.

Furthermore, surprisingly it was found that the terminal halogen atoms of the multivalent esters of the general Formula (X) can be replaced by nucleophilic reagents such as phenols more readily and within considerably shorter time than those of the simple esters of the general Formula (VI) mentioned above. Thus, if the compounds of the general Formula (X) are reacted with 2,5-dimethylphenol or with a salt thereof, multivalent esters of the general Formula (XI)

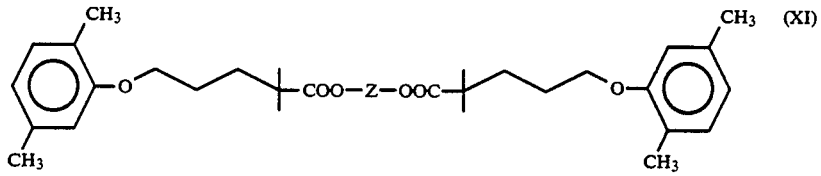
(XI)

are obtained, wherein Z is as given for the general Formula (VIII), except that if Z in this latter contains hydroxy group(s), then Z in the compound of the general Formula (XI) contains 2,2-dimethyl-5-(2,5-dimethylphenoxy)-pentanoyloxy group(s) at the corresponding site(s). The compounds of the general Formula (XI) thus obtained can be isolated, if desired, by methods known per se, but it is preferable to hydrolize them into the desired compound of Formula (I) directly in the same reaction mixture in which they were formed. The hydrolysis is carried out by methods known per se and surprisingly it proceeds within shorter time than in case of the known esters of the general Formula (V).

In addition, most surprisingly it was found that substitution of 2,5-dimethylphenoxy groups for the terminal halogen atoms in the multivalent esters of the general Formula (X) can be carried out still more readily, under very mild reaction conditions and within very short reaction time, if the latter compounds are allowed to react with an ester of 2,5-dimethylphenol formed with a lower alkanoic acid, i.e. with a compound of the general Formula (XV)

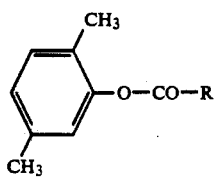

$$(XV)$$

wherein R stands for $C_{1-5}$ alkyl, in a polar aprotic solvent, in the presence of a strong base, to afford the compounds of the general Formula (XI) mentioned above.

Only scattered examples can be found in the literature for reactions of this type, i.e. formation of an aryl alkyl ether by reaction of an aryl ester with an alkyl halide [e.g. S. F. McDonald, J. Chem. Soc. 1948, 376; S. K. Banerjee, J. Chem. Soc. Chem. Commun. 1982, 815; and A. Yamashita and A. Toy, Synth. Commun 19, 755 (1989)]. It is, however, pointed out that in the known examples mentioned above the ether is formed at reflux temperature of the reaction mixture or by prolonged (24-48 hours) stirring at ambient temperature. By contrast, in the process of the present invention the reaction of the aryl esters of the general Formula (XV) with the halogenated multivalent esters of the general Formula (X) is completed, without external heating, in less than 10 minutes. The advantages of this latter method are further illustrated by the fact that under identical reaction conditions the alkali salt of 2,5-dimethylphenol afforded the final product of Formula (I) with a 20% lower yield.

Thus, according to an aspect of the present invention there is provided a process for the preparation of 2,2-dimethyl-5-(2,5-dimethylphenoxy)-pentanoic acid of Formula (I), which comprises reacting an ester of the general Formula (X), wherein X represents halogen such as chlorine, bromine or iodine, and Z stands for a straight or branched chain $C_{1-8}$ alkylene group optionally substituted by one or two 2,2-dimethyl-5-halopentanoyloxy group(s), wherein halo represents chlorine or bromine, and in which alkylene group one or two methylene group(s) may be optionally replaced either by hetero atom(s), preferably oxygen and/or nitrogen atom(s), which latter may be optionally substituted by phenyl or $C_{1-4}$ alkyl optionally substituted by a 2,2-dimethyl-5-halopentanoyloxy group; or by a bivalent heterocyclic group such as piperazine-1,4-diyl group, with an alkali salt of 2,5-dimethylphenol of Formula (II), optionally in the presence of an alkali iodide as catalyst, and hydrolizing the aryloxy-substituted ester of the general Formula (XI) thus obtained, wherein Z stands for a straight or branched chain $C_{1-8}$ alkylene group optionally substituted by one or two 2,2-dimethyl-5-(2,5-dimethylphenoxy)-pentanoyloxy group(s), in which alkylene group one or two methylene group(s) may be optionally replaced either by hetero atom(s), preferably oxygen and/or nitrogen atom(s), which latter may be optionally substituted by phenyl or $C_{1-4}$ alkyl optionally substituted by a 2,2-dimethyl-5-(2,5-dimethylphenoxy)-pentanoyloxy group; or by a bivalent heterocyclic group such as piperazine-1,4-diyl group, optionally without isolation, directly in the reaction mixture in which it was formed.

According to another aspect of the present invention there is provided a process for the preparation of 2,2-dimethyl-5-(2,5-dimethylphenoxy)-pentanoic acid of Formula (I), which comprises reacting a multivalent ester of the general Formula (X), wherein X represents halogen such as chlorine, bromine or iodine, and Z stands for a straight or branched chain $C_{1-8}$ alkylene group optionally substituted by one or two 2,2-dimethyl-5-halopentanoyloxy group(s), wherein halo represents chlorine or bromine, and in which alkylene group one or two methylene group(s) may be optionally replaced by hetero atom(s), preferably oxygen and/or nitrogen atom(s), which latter may be optionally substituted by phenyl or $C_{1-4}$ alkyl optionally substituted by a 2,2-dimethyl-5-halopentanoyloxy group, with a 2,5-dimethylphenyl ester of the general Formula (XV), wherein R stands for $C_{1-5}$ alkyl, in a polar, aprotic solvent, in the presence of a strong base and optionally in the presence of an alkali iodide as catalyst, and hydrolyzing the aryloxy substituted multivalent ester of the general Formula (XI) thus obtained, wherein Z stands for a straight or branched chain $C_{1-8}$ alkylene group optionally substituted by one or two 2,2-dimethyl-5-(2,5-dimethylphenoxy)-pentanoyloxy group(s), in which alkylene group one or two methylene group(s) may be optionally replaced by hetero atom(s), preferably oxygen and/or nitrogen atom(s), which latter may be optionally substituted by phenyl or $C_{1-4}$ alkyl optionally substituted by a 2,2-dimethyl-5-(2,5-dimethylphenoxy)-pentanoyloxy group, optionally without isolation, directly in the reaction mixture in which it was formed.

According to a preferred embodiment of the present invention a new multivalent ester of the general Formula (X) is reacted with the potassium or sodium salt of 2,5-dimethylphenol. The salt can be prepared either in a separate operation or in situ. If it is prepared in a separate operation, one may proceed e.g. by adding an appropriate potassium or sodium compound (such as sodium hydroxide, potassium hydroxide, sodium carbonate, potassium carbonate, sodium hydride, etc.) to a solution of 2,5-dimethylphenol in an appropriate solvent (e.g. in methanol, ethanol, propanol, butanol, tetrahydrofuran, acetonitrile and the like). The mixture is then stirred until complete dissolution and the solvent is distilled off. The salt thus obtained can be used directly for the next reaction step.

If the salt is prepared in situ, the salt formation can also be carried out with the sodium or potassium compound mentioned above. As solvent e.g. polar solvents (such as dimethylformamide or dimethyl acetamide) or alcohols (such as ethanol, n-propanol or n-butanol) can be used. If the salt is formed by using sodium hydroxide, the water formed during neutralization may optionally be removed from the reaction mixture by a suitable method, but the next reaction step can also be performed without removing the water. If desired, the water can be removed e.g. by azeotropic distillation. In this case the salt formation is carried out in a solvent useful for the said distillation, such as benzene, toluene, xylene, chlorobenzene and the like.

For the further reaction of the phenol salt thus obtained it may be desirable that at least a part of it be dissolved. For this purpose a strongly polar auxiliary solvent (such as dimethylformamide, dimethyl sulfoxide, dimethyl acetamide, hexamethylphosphorous triamide, N-methylpyrrolidone and the like) can be added to the above-mentioned solvents in an amount of about 5 to 30% by vol. related to the other solvent. The salt of the phenol of Formula (II) can be reacted with the intermediate of general Formula (X) preferably in the presence of an alkali iodide (e.g. sodium or potassium iodide) as catalyst at a temperature between about 70° and 130° C. Thus the reaction is completed within 1 to 3 hour(s). The aryloxy-substituted multivalent ester thus obtained can be isolated by methods known per se, e.g. by solvent extraction, decolourization and/or chromatography, and then subjected to hydrolysis in a separate operation, but it is preferable to carry out the hydrolysis in situ and to isolate only the final product of Formula (I) thus obtained. The hydrolysis can be carried out either in acidic or in basic reaction medium, preferably by using an alkali hydroxide, such as sodium hydroxide. The final product can be isolated and purified by conventional methods (e.g. solvent extraction and then decolourization and crystallization).

It was found that the isolation of the final product according to U.S. Pat. No. 4,665,226, that is acidification of a strongly alkaline aqueous solution followed by filtration, afford a more contaminated product than our variant of the isolation in which the acidification is performed in the presence of an appropriate organic solvent and thus the product is transferred into the organic phase followed by a first purification by decolourization. For the decolourization e.g. active carbon, silica gel, aluminium oxide and the like can be used. After concentration of the decolourized solution a crude product is obtained which can be purified by a simple recrystallization to yield the final product in the purity required by the U.S. Pharmacopoeia. The recrystallization can be carried out by using various solvents, e.g. acetone, 2-butanone, 3-pentanone, 4-heptanone, acetonitrile, ethyl acetate, n-hexane, methanol, ethanol, isopropanol, 2-mehoxyethanol, 2-ethoxyethanol and the like. In case of water-miscible solvents the aqueous mixture thereof can also be applied.

According to another preferred embodiment of the present invention a multivalent ester of the general Formula (X) is reacted with a 2,5-dimethylphenyl ester of the general Formula (XV) in a polar aprotic solvent, in the presence of a strong base and optionally in the presence of an alkali iodide as catalyst. Suitable solvents are e.g. dimethyl sulfoxide, dimethylformamide, dimethylacetamide, sulfolane, hexamethyl phosphoric triamide, N-methylpyrrolidone and the like, the preferred solvent being dimethyl sulfoxide. The solvent should not necessarily be anhydrous, a water content below 1 % v/v exerts no harmful effect upon the reaction. Suitable bases include hydroxides and alkoxides of alkali metals, e.g. sodium hydroxide, potassium hydroxide, sodium methoxide, sodium ethoxide, potassium tert-butoxide and the like. Preferably potassium tert-butoxide is used.

The base has two functions in this process. First, it promotes the reaction of the compound of the general Formula (XV) with the compound of the general Formula (X). For this purpose 1-4 mole equivalents, preferably 2-3 mole equivalents, of the base calculated upon the compound of the general Formula (XV) is used. After completion of the ether formation, another portion (about the same amount as above) of the base is added to the reaction mixture, along with 2-5 mole equivalents of water, calculated upon the compound of the general Formula (XV), in order to initiate hydrolysis.

When X in the compound of the general Formula (X) stands for other than iodine atom, the reaction is preferably carried out in the presence of 0.2-2.0 mole equivalents of sodium iodide or potassium iodide calculated upon the compound of the general Formula (X).

The reaction is performed by mixing the reagents at room temperature (at this point a slightly exothermic reaction occurs) followed by stirring the reaction mixture without external heating until ether formation followed by TLC is completed. This requires 5-10 minutes (cf. the earlier methods where the alkali salt of 2,5-dimethylphenol reacted with an appropriate halide at 110°-50° C. within 6-13 hours). If desired, the obtained aryloxy substituted ester of the general Formula (XI) can be isolated and hydrolysed to the final product of Formula (I) in a separate operation, as mentioned above, but this hydrolysis is preferably carried out in situ by adding an additional amount of the base plus water and stirring the reaction mixture at room temperature. Surprisingly, under such conditions the hydrolysis is completed within about 1 hour, in contrast with the earlier methods in which hydrolysis of the analogous intermediates required 4-6 hours at 110°-150° C.

The final product of Formula (I) can be isolated and purified by conventional methods as described above.

The procedure discussed above affords Gemfibrozil in high purity which complies with the requirements of the U.S. Pharmaceopoeia and with yields comparable with that of the most favourable known method (U.S. Pat. No. 4,665,226).

The starting aryl esters of the general Formula (XV) are known or can be prepared by known methods [e.g. F. D. Chattaway, J. Chem. Soc. 1931, 2495; E. Baumgarten, J. Am. Chem. Soc. 66, 303 (1944)] starting with 2,5-dimethylphenol, in excellent yields.

According to a further aspect of the present invention there are provided new intermediates of the general Formula (X), wherein X and Z are as stated above.

Preferred representatives of the new compounds of the general Formula (X) are the following derivatives:
1,3-bis(2,2-dimethyl-5-chloropentanoyloxy)-propane,
1,3-bis(2,2-dimethyl-5-iodopentanoyloxy)-propane,
1,6-bis(2,2-dimethyl-5-chloropentanoyloxy)-hexane, and bis[2-(2,2-dimethyl-5-chloropentanoyloxy)-ethyl]-ether.

According to a still further aspect of the present invention there is provided a process for the preparation of new multivalent esters of the general Formula (X), which comprises a) reacting a multivalent alcohol of the general Formula (VIII), wherein Z stands for a straight or branched chain $C_{1-8}$ alkylene group optionally substituted by one or two hydroxy group(s), and in which alkylene group one or two methylene group(s) may be optionally replaced either by hetero atom(s), preferably oxygen and/or nitrogen atom(s), which latter may be optionally substituted by phenyl or $C_{1-4}$ alkyl optionally substituted by a hydroxy group, or by a bivalent heterocyclic group such as piperazine-1,4-diyl group, or an activated derivative thereof with isobutyric acid, and reacting the ester of the general Formula (IX) thus obtained, wherein Z is as stated for the general Formula (VIII), except that if Z in this latter contains hydroxy group(s) then Z in the compound of the general Formula (IX) contains 2-methylpropanoyloxy group(s) at the corresponding site(s), with a 1,3-dihalopropane in an aprotic organic solvent, in the presence of a strong organic base; or b) reacting 2,2-dimethyl-4-pentenoic acid of the Formula (XII)

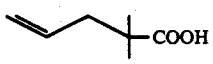

(XII)

with a multivalent alcohol of the general Formula (VIII), wherein Z is as stated in the above variant a), or with an activated derivative thereof, and adding a hydrogen halide to the double bonds of the ester of the general Formula (XIII)

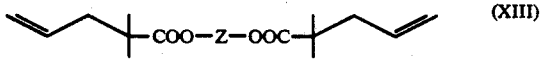

(XIII)

thus obtained, wherein Z is as stated for the general Formula (VIII) in the above variant a), except that if Z in this latter contains hydroxy group(s), then Z in the compound of the general Formula (XIII) contains 2,2-dimethyl-4-pentenoyloxy group(s) at the corresponding site(s), in an apolar solvent, optionally in the presence of a catalyst suitable to promote radical reactions; or c) reacting a carboxylic acid of the general Formula (XIV),

(XIV)

wherein X stands for halogen, with a multivalent alcohol of the general Formula (VIII), wherein Z is as given in variant a), or with an activated derivative thereof; or d) reacting a multivalent ester of the general Formula (IX), wherein Z is as stated for the general Formula (VIII) in the above variant a), except that if Z in this latter contains hydroxy group(s), then Z in the compound of the general Formula (IX) contains 2-methylpropanoyl group(s) at the corresponding site(s), with a 1,3-dihalopropane in an aprotic organic solvent, in the presence of a strong organic base; or e) adding a hydrogen halide to the double bonds of an ester of the general Formula (XIII), wherein Z is as stated for the general Formula (VIII) in the above variant a), except that if Z in this latter contains hydroxy group(s), then Z in the compound of the general Formula (XIII) contains 2,2-dimethyl-4-pentenoyloxy group(s) at the corresponding site(s), in an organic solvent, in the presence of a catalyst suitable to promote radical reactions.

According to variant a) of the process for the preparation of compounds of the general Formula (X), in the first step the multivalent alcohols of the general Formula (VIII) are esterified with isobutyric acid in an appropriate solvent, in the presence of an acidic catalyst, to obtain the multivalent esters of the general Formula (IX). As solvent any inert solvent can be used but it is preferable to choose a solvent by the aid of which the water formed during the reaction can optionally by removed by azeotropic distillation. In this way the equilibrium of the reaction can be shifted toward formation of the multivalent esters of the general Formula (IX). Such solvents are e.g. benzene, toluene, xylene, 1,2-dichloroethane and the like. As catalyst inorganic acids (such as hydrogen chloride, hydrogen bromide, sulfuric acid) or organic acids (such as acetic acid, p-toluenesulfonic acid etc.) can be used.

The compounds of the general Formula (IX) can also be prepared by reacting the alcohols of the general Formula (VIII) with isobutyric acid in the presence of a condensing agent, e.g. a carbodiimide (such as N,N'-dicyclohexylcarbodiimide).

Besides, the activated derivatives of the multivalent alcohols of the general Formula (VIII) can also be used for the preparation of the esters of the general Formula (IX). Preferred activated derivatives of the multivalent alcohols of the general Formula (VIII) include the esters thereof formed with aliphatic or aromatic sulfonic acids or with hydrogen halogenides, which can be reacted with a metal salt of isobutyric acid. Similarly, the activated derivatives of the isobutyric acid (e.g. the anhydride, halogenides, mixed anhydrides formed with other acids and activated esters) can also be used for the preparation of the compounds of the general Formula (IX).

The multivalent esters of the general Formula (IX) thus obtained can be isolated and purified by methods known per se, e.g. by solvent extraction, decolourization and/or distillation.

The starting multivalent alcohols of the general Formula (VIII) are known and commercially available products or can be prepared by known methods.

In the second reaction step according to variant a) a compound of the general Formula (IX) is reacted with a 1,3-dihalopropane in an aprotic organic solvent, in the presence of a strong organic base. As aprotic organic solvent any solvent usually applied for carbanionic reactions (e.g. tetrahydrofuran and/or hexamethylphosphoric triamide, further dioxane, diethyl ether, 1,2-dimethoxyethane, bis(2-methoxyethyl)-ether and the like, or the mixture thereof) can be used. Preferably tetrahydrofuran, hexamethylphosphoric triamide or mixtures thereof are used. Suitable organic bases include the salts of alkali metals (such as lithium, sodium or potassium) formed with a dialkylamine, wherein alkyl is lower alkyl. Especially preferred organic base is the lithium diisopropylamide which can be prepared in situ by known methods either from an organic lithium compound (such as n-butyllithium) or from lithium metal by reaction with diisopropylamine. If lithium metal is used for this reaction, an appropriate diene (e.g. styrene, alpha-methylstyrene, naphtalene etc.) is used as auxiliary agent (J. Mulzer et al.: Tetrahedron 40, 2211 [1984]; M. T. Reetz and W. F. Maier: Annalen 1980, 1471; K. Ziegler: Annalen 511, 64 [1934]).

The temperature of both reactions, namely that of the multivalent ester of the general Formula (IX) with the above-mentioned strong base (whereby the ester is deprotonated at the alpha carbon atoms of the acyl groups to form a carbanion) and the subsequent alkylation, may vary between $-20°$ C. and $100°$ C., preferably between $0°$ C. and $30°$ C. Under such conditions the reaction proceeds within 3 to 30 hours, but when applying the esters of the general Formula (IX), obtained from the preferable alcohols of the general Formula (VIII) listed above, the alkylation is complete within 3 hours. The compound of the general Formula (X) thus obtained can be separated and purified by methods known per se, e.g. by solvent extraction, decolourization and chromatography, but crude compounds of the general Formula (X) can also be used in the next reaction step.

In the first step according to variant b) 2,2-dimethyl-4-pentenoic acid of Formula (XII) (prepared e.g. by the method described in published European patent application No. 219,117) is esterified with a multivalent alcohol of the general Formula (VIII) to obtain a multivalent ester of the general Formula (XIII). This latter contains, depending on the number of the hydroxy groups in the starting alcohols of the general Formula (VIII), at least two, optionally three or four 2,2-dimethyl-4-pentenoyloxy groups. The reaction can be performed by using any of the methods specified above for the first step of variant a).

According to the second step of variant b) a hydrogen halide is added to the double bonds of an ester of the general Formula (XII). This reaction can be carried out in an appropriate solvent, e.g. in a hydrocarbon (such as benzene, pentane, hexane, heptane, cyclohexane and the like), optionally in the presence of a catalyst promoting radical reactions [e.g. dibenzoyl peroxide, azo-bis(2-methylpropionitrile) etc.], at a temperature between about $-30°$ C. and $+30°$ C. Under such conditions the halogen atom of the hydrogen halide is attached selectively to the terminal carbon atom, and thus the intermediates of the general Formula (X) are obtained. As hydrogen halide preferably hydrogen bromide is used.

The 2,2-dimethyl-4-pentenoic acid of Formula (XII) used as starting substance in variant b) is a known compound. It can be prepared in two steps with an excellent yield, e.g. by the method described in published European patent application No. 219,117, starting with isobutyric acid.

On the other hand, the sequence of the above two reaction steps, namely the esterification and the addition, can be reversed. Consequently, one may also proceed by adding first a hydrogen halide to the double bond of the 2,2-dimethyl-4-pentenoic acid of the formula (XII) (e.g. according to the method described in pubished European patent application No. 219,117), and then esterifying the 2,2-dimethyl-5-halopentenoic acid of the general Formula (XIV) thus obtained by methods known per se, with a multivalent alcohol of the general Formula (VIII) or with an activated derivative thereof. This version corresponds to variant c) for the preparation of compounds of the general Formula (X).

The compounds of the general Formula (X) wherein X stands for iodine, can also be prepared by halogen exchange reaction, starting with the corresponding chloro or bromo compounds obtained as described above, and refluxing the latter with 1-3 mole equivalent(s) of an alkali iodide, e.g. sodium iodide or potassium iodide, in a suitable solvent, e.g. in acetone or acetonitrile, for 5-15 hours, followed by isolation of the product by any conventional method. The purity of the compounds of the general Formula (X) can be analysed e.g. by gas chromatography.

The present invention encompasses all the reaction variants using any of the intermediates mentioned above as starting substance and carrying out the remaining reaction steps.

The new process according to the invention is more advantageous than the hitherto known methods serving for the preparation of Gemfibrozil.

If the intermediate of the general Formula (X) is prepared according to variant a) above, and this intermediate is allowed to react either with an alkali metal salt of 2,5-dimethylphenol or with an ester of the latter formed with a lower alkanoic acid, the total yield of the final product of Formula (I) calculated upon isobutyric acid falls in the same range as when the best hitherto known method provided in U.S. Pat. No. 4,665,226 is followed. The quality of the product obtained according to the known method is, however, unsuitable for direct pharmaceutical use, while the process according to the invention yields the product in the purity required by U.S. Pharmacopoeia. Besides, variant a) of the process for the preparation of the compounds of the general Formula (X) has technological advantages, too, which provide a more economic production of Gemfibrozil on industrial-scale than even the best known method. Thus 1. the process is based on the intermediates of the general Formula (IX), which can be more readily purified and dried than the lower alkyl esters of isobutyric acid;
2. the intermediates of the general Formula (X) obtained in the second reaction step can be used in the next reaction step without purification;
3. the second step of variant a) and the reaction resulting in Gemfibrozil of Formula (I), respectively, proceed within considerably shorter time than the process according to the U.S. patent specification mentioned above, wherein isobutyl isobutyrate is used as starting substance.

The reaction times of the individual reaction steps are compared as follows:

|  | Starting with isobutyl isobutyrate (according to U.S. patent specification No. 4,665,226) | Starting with the esters of the general Formula (IX) |
|---|---|---|
| Alkylation with 1-bromo-3-chloropropane | 13 hours | 3 hours |
| Reaction of the chloropropylated intermediate with the phenol salt | 13 hours | 2 hours |
| Reaction of the chloropropylated intermediate with the 2,5-dimethylphenyl ester | — | 10 minutes |
| Hydrolysis of the ester of the final roduct | 4 hours | 1-2 hour(s) |

From the above data it can be established that the application of the process according to the invention—compared with the best known method—results in considerable savings in time.

Further details of the process are given in the following Examples which do not intend to limit the scope of the invention.

The preparation of the compound of Formula (I) by reaction of the intermediates of the general Formula (X) with an alkali salt of 2,5-dimethylphenol is illustrated by Examples 1-24. Examples 25-44 relate to the synthesis of the new intermediates of the general Formula (X), while the reaction of the latter compounds with the aryl esters of the general Formula (XV) is illustrated by Examples 45-53.

EXAMPLE 1

2,2-Dimethyl-5-(2,5-dimethylphenoxy)-pentanoic acid

To a mixture of 6.92 g (0.048 mole) of sodium 2,5-dimethylphenoxide, 50 ml of dimethylformamide and 0.75 g (0.005 mole) of sodium iodide 9.0 g (0.0253 mole) of pure 1,2-bis(2,2-dimethyl-5-chloropentanoyloxy)-ethane (X) prepared as described in step b) of Example 25 are added at about 100° C., and the mixture is stirred at a temperature between 115° C. and 120° C. for 2 hours. Then it is cooled to about 100° C., 4.0 g (0.1 mole) of sodium hydroxide and 2 ml of water are added and the mixture is stirred for 2 hours at a temperature between 115° C. and 120° C. Then further 4.0 g (0.1 mole) of sodium hydroxide are added at about 100° C., and stirring is continued at a temperature between 115° C. and 120° C. for further 2 hours. The reaction mixture is cooled to room temperature, poured onto 150 ml of water and washed twice with 30 ml of toluene each. The aqueous phase is acidified with 20% hydrochloric acid to pH=1 in the presence of 50 ml of hexane while cooled in an ice bath, the aqueous phase is separated and extracted twice with 30 ml of hexane each. The hexane phases are combined, washed three times with 30 ml of water, and the solvent is distilled off under reduced pressure. Thus 9.9 g of the desired compound are obtained in the form of an almost colourless solid substance. Yield: 82.4 %. M.p.: 48°-54° C. The crude product is recrystallized from 20 ml of a 7:3 mixture of methanol and water. In this way 8.4 g of the title compound are obtained in the form of colourless crystals. Yield: 70.0 %, m.p.: 57°-58 ° C. The purity of the thus-obtained product complies with the requirements prescribed in U.S. Pharmacopoeia XXII. The total yield in two reaction steps calculated upon the starting substance of step b) of Example 25, i.e. upon 1,2-bis(2-methyl-propanoyloxy)-ethane (IX), is 49.0%. The total yield in three reaction steps [steps a) and b) of Example 25+Example 1] calculated upon ethylene glycol (VIII) amounts to 41.7%.

The sodium salt of 2,5-dimethylphenol used in the above reaction can be prepared e.g. by the following methods:

Method A)

To a solution of 12.2 g (0.1 mole) of 2,5-dimethylphenol in 100 ml of ethanol 4.1 g (0.1 mole) of solid sodium hydroxide of 98% purity are added at room temperature, and the reaction mixture is stirred until dissolution is complete. The solvent is distilled off under reduced pressure and the residue is dried in an exsiccator to constant weight. Thus 14.4 g of the desired product are obtained in the form of a solid grey substance. Yield: 100%, m.p.>250° C.

Method B)

To 100 ml of tetrahydrofuran 0.9 g (0.03 mole) of 80% sodium hydride are added at room temperature, under stirring followed by 3.66 g (0.03 mole) of 2,5-dimethylphenol. The mixture is stirred for 30 minutes at room temperature, then for another 30 minutes under reflux. The solvent is distilled off under reduced pressure, the solid residue is washed with benzene and dried under reduced pressure. Thus 3.64 g of the desired compound are obtained.
Yield: 82%.

EXAMPLE 2

2,2-Dimethyl-5-(2,5-dimethylphenoxy)-pentanoic acid

The procedure described in Example 1 is followed except that 1,2-bis(2,2-dimethyl-5-chloropentanoyloxy)-ethane (X) prepared according to step b) of Example 26 is used as starting substance. In this manner the yield of the obtained pure title product is 67.1%. The total yield of the product in two reaction steps calculated upon 1,2-bis(2-methylpropanoyloxy)-ethane (IX), the starting material of step b) of Example 26, amounts to 39.7%. The total yield in three reaction steps [steps a) and b) of Example 26+Example 2] calculated upon ethylene glycol amounts to 33.8%.

EXAMPLE 3

2,2-Dimethyl-5-(2,5-dimethylphenoxy)-pentanoic acid

The procedure described in Example 1 is followed except that instead of 1,2-bis(2,2-dimethyl-5-chloropentanoyloxy)-ethane 12.0 g (0.025 mole) of crude 1,3-bis(2,2-dimethyl-5-chloropentanoyloxy)-propane (X) of 77% purity, prepared according to step b) of Example 27, are used. Thus the total yield of the crude product in two reaction steps calculated upon 1,3-bis(2-methylpropanoyloxy)-propane (IX) amounts to 55.2%. After recrystallization from a 7:3 mixture of ethanol and water the desired compound is obtained in pure form with a yield of 41.4%. The total yield in three reaction steps [steps a) and b) of Example 27+Example 3] calculated upon 1,3-propanediol (VIII) amounts to 36.1%.

If n-butanol is used as solvent instead of dimethylformamide, the desired compound is obtained in a yield of 29.5% calculated upon the starting substance of step b) of Example 27, and the total yield in three reaction steps amounts to 25.7%.

EXAMPLE 4

2,2-Dimethyl-5-(2,5-dimethylphenoxy)-pentanoic acid

Step a)

1,3-Bis[2,2-dimethyl-5-(2,5-dimethylphenoxy)-pentanoyloxy]-propane (XI)

To a mixture of 2.9 g (0.02 mole) of sodium 2,5-dimethylphenoxide, 50 ml of dimethylformamide and 0.3 g (0.002 mole) of sodium iodide 5.0 g (0.0104 mole) of crude 1,3-bis(2,2-dimethyl-5-chloropentanoyloxy)-propane (X) prepared according to step b) of Example 27 are added at 100° C., under stirring. The mixture is stirred at a temperature between 115° C. and 120° C. for 2 hours, cooled, poured onto 150 ml of water and extracted three times with 30 ml of toluene. The toluene phase is extracted three times with 10 ml of ice-cold 1N sodium hydroxide solution, washed with water until neutral, dried over sodium sulfate and the solvent is distilled off at reduced pressure. Thus 4.74 g of the desired diester are obtained in the form of a dark yellow oil. The yield calculated upon the starting substance of step b) of Example 27 amounts to 64.9%. The thus-obtained product is purified by chromatography on a silica gel column eluted with a 80:20 mixture of hexane and diethyl ether to give 2.63 g of the desired compound in analytically pure state. According to TLC developed with the above solvent mixture $R_f=0.5$. The yield calculated upon the starting substance of step b) of Example 27 amounts to 36.0%.

Step b)

2.2-Dimethyl-5-(2,5-dimethylphenoxy)-pentanoic acid 10.8 g (0.02 mole) of pure diester obtained according to step a) above are added to a mixture of 200 ml of ethanol and 50 ml of 2N aqueous sodium hydroxide solution, and the reaction mixture is heated under reflux for 3 hours. Then it is cooled, the bulk of the ethanol is distilled off under reduced pressure, the residue is diluted with 200 ml of water and washed twice with 50 ml of diethyl ether. The diethyl ether phase is dried over sodium sulfate and the solvent is distilled off to recover 0.5 g of unreacted starting substance. The aqueous phase is freed of organic solvent under reduced pressure and the aqueous solution is acidified to pH=1 with 20% hydrochloric acid. The precipitated desired compound is filtered, washed with water and dried at room temperature to give 7.9 g of a product melting at 56°–57° C. Yield: 82.0%. The total yield in four reaction steps [steps a) and b) of Example 27+steps a) and b) of Example 4] based on 1,3-propanediol (VIII) amounts to 25.7%.

EXAMPLE 5

2,2-Dimethyl-5-(2,5-dimethylphenoxy)-pentanoic acid

To a mixture of 4.89 g (0.04 mole) of 2,5-dimethylphenol and 100 ml of dimethylformamide 1.26 g (0,042 mole) of 80% sodium hydride are added under stirring, and the reaction mixture is stirred at 50°–60° C. until no more gas is evolved (about 20 minutes). After heating to about 100° C. 0.6 g (0.004 mole) of sodium iodide and 9.6 g (0.02 mole) of crude 1,3-bis(2,2-dimethyl-5-chloropentanoyloxy)-propane (X) prepared according to step b) of Example 27 are successively added. The mixture is stirred at a temperature between 115° C. and 120° C. for 2 hours, then after cooling to 100° C. 3.2 g (0.08 mole) of sodium hydroxide and 2 ml of water are added and stirring is continued at a temperature between 115° C. and 120° C. for further 2 hours. Then 3.2 g (0.08 mole) of sodium hydroxide are added at 100° C. and stirring is continued again at 115°–120 ° C. for further 2 hours. The reaction mixture is worked up as described in Example 1. Thus 5.3 g of the desired compound are obtained. Yield [calculated upon 1,3-bis(2-methylpropanoyloxy)-propane]: 40.8%. The total yield in three reaction steps [steps a) and b) of Example 27+Example 5] calculated upon 1,3-propanediol amounts to 35.6%.

EXAMPLE 6

2,2-Dimethyl-5-(2,5-dimethylphenoxy)-pentanoic acid

To a mixture of 4.4 g (0.036 mole) of 2,5-dimethylphenol, 50 ml of n-butanol and 1.6 g (0.04 mole) of sodium hydroxide 0.54 g (0.0036 mole) of sodium iodide and 8.7 g (0.018 mole) of crude 1,3-bis(2,2-dimethyl-5-chloropentanoyloxy)-propane (X) prepared according to step b) of Example 27 are successively added at about 100° C. The reaction mixture is stirred for 2 hours under reflux, cooled to 90° C. and 2.88 g (0.072 mole) of sodium hydroxide are added. Stirring is continued under reflux for further 2 hours, then the solvent is distilled off under reduced pressure. The residue is dissolved in 100 ml of water and extracted twice with 20 ml of toluene each. The aqueous phase is acidified with 20% hydrochloric acid to pH=1 in the presence of 50 ml of hexane while cooling in an ice bath, the aqueous phase is separated and extracted two times with 30 ml of hexane each. The hexane extracts are combined, washed three times with 30 ml of water, dried over sodium sulfate, decolourized with 0.5 g of silica gel and the solvent is distilled off under reduced pressure. Thus 4.9 g of crude product are obtained in solid form in a yield of 41.6% [calculated upon 1,3-bis(2,2-dimethyl-5-chloropentanoyloxy)-propane (X)]. After recrystallization from acetonitrile 3.05 g of the desired compound are obtained in pure form in a yield of 25.9%. The total yield in three reaction steps [steps a) and b) of Example 27+Example 6] calculated upon 1,3-propanediol (VIII) amounts to 22.6%.

EXAMPLE 7

2,2-Dimethyl-5-(2,5-dimethylohenoxy)-pentanoic acid

A mixture of 9.41 g (0.077 mole) of 2,5-dimethylphenol, 3.3 g (0.0825 mole) of sodium hydroxide, 100 ml of toluene and 10 ml of dimethyl sulfoxide is stirred under reflux for 2 hours while the water being formed is continuously separated by using a Dean-Stark apparatus. Then 1.16 g (0.0077 mole) of sodium iodide and 18.5 g (0.0385 mole) of crude 1,3-bis(2,2-dimethyl-5-chloropentanoyloxy)-propane (X) prepared according to step b) of Example 27 are successively added. The reaction mixture is stirred under reflux for 2 hours, cooled to about 100° C. and 5.8 g (0.145 mole) of sodium hydroxide are added. Stirring under reflux is continued for further 2 hours, then the mixture is cooled, 100 ml of water are added, the aqueous phase is separated and washed twice with 30 ml of toluene. The mixture is then acidified with 40 ml of 20% hydrochoric acid to pH=1 in the presence of 100 ml of hexane while cooling in an ice bath. The aqueous phase is separated, extracted twice with 30 ml of hexane each, the hexane phases are combined, washed three times with 30 ml of water each and dried over sodium sulfate. The dried solution is decolourized by stirring with 1 g of silica gel for 30 minutes, then the solvent is distilled off under reduced pressure. Thus 15.8 g of crude product are obtained in the form of an almost colourless solid. Yield [based on 1,3-bis(2-methyl-propanoyloxy)-propane (IX) in two reaction steps]: 63.0%. After recrystallization from 32 ml of a 7:3 mixture of methanol and water 13.1 g of the desired compound are obtained in pure form. M.p.: 56°–58° C. The yield in two reaction steps calculated upon the starting compound of step b) of Example 27 amounts to 52.3%. The total yield in three reaction steps [steps a) and b) of Example 27+Example 7] calculated upon 1,3-propanediol (VIII) amounts to 45.6%.

EXAMPLE 8

2,2-Dimethyl-5-(2,5-dimethylphenoxy)-pentanoic acid

The procedure described in Example 7 is followed except that 1,3-bis(2,2-dimethyl-5-chloropentanoyloxy)-propane (X) prepared as described in step b) of Example 28 is used as starting substance. Thus the total yield of the product in three reaction steps [steps a) and b) of Example 28+Example 8] based on 1,3-propanediol (VIII) amounts to 32.8%.

EXAMPLE 9

2,2-Dimethyl-5-(2,5-dimethylohenoxy)-pentanoic acid

The procedure described in Example 7 is followed except that 1,3-bis(2,2-dimethyl-5-chloropentanoyloxy)-propane (X) purified according to step b) of Example 29 is used as starting substance. Thus, after recrystallization, the desired compound is obtained in a yield of 64.6% calculated upon 1,3-bis(2,2-dimethyl-5-chloropentanoyloxy)-propane (X). The total yield in three reaction steps [steps a) and b) of Example 29+Example 9] calculated upon 1,3-propanediol amounts to 43.0%.

EXAMPLE 10

2,2-Dimethyl-5-(2,5-dimethylphenoxy)-pentanoic acid

The procedure described in Example 7 is followed except that 19.5 g (0.019 mole) of crude 1,3-bis(2,2-dimethyl-5-chloropentanoyloxy)-propane prepared according to step b) of Example 30 are used as starting substance. Thus the desired compound is obtained in a yield of 32.8% calculated upon the starting substance of step b) of Example 30. The total yield in three reaction steps [steps a) and b) of Example 30+Example 10] based on 1,3-propanediol (VIII) is 28.6%.

EXAMPLE 11

2,2-Dimethyl-5-(2,5-dimethylphenoxy)-pentanoic acid

The procedure described in Example 7 is followed except that crude 1,3-bis(5-bromo-2,2-dimethylpentanoyloxy)-propane (X) prepared as described in step b) of Example 31 is used as starting substance, instead of 1,3-bis(2,2-dimethyl-5-chloropentanoyloxy)-propane. Thus the desired compound is obtained in the form of colourless crystals in a yield of 37.0% in two reaction steps calculated upon 1,3-bis(2,2-dimethyl-4-pentenoyloxy)-propane (XIII). After recrystallization from a 7:3 mixture of ethanol and water the pure desired compound is obtained in a yield of 20.4%. The total yield in three reaction steps [steps a) and b) of Example 31+Example 11] calculated upon 2,2-dimethyl-4-pentenoic acid (XII) amounts to 14.0%.

EXAMPLE 12

2,2-Dimethyl-5-(2,5-dimethylphenoxy)-pentanoic acid

The procedure described in Example 7 is followed with the difference that crude 1,2-bis(2,2-dimethyl-5-bromopentanoyloxy)-ethane prepared according to step b) of Example 32 is used as starting substance, instead of 1,3-bis(2,2-dimethyl-5-chloropentanoyloxy)-propane. Thus the desired compound is obtained in the form of colourless crystals in a yield of 30% in two reaction steps calculated upon 5-bromo-2,2-dimethylpentanoic acid (XIV).

EXAMPLES 13 to 24

2,2-Dimethyl-5-(2,5-dimethylohenoxy)-pentanoic acid

The procedure described in Example 7 is followed except that instead of 1,3-bis(2,2-dimethyl-5-chloropentanoyloxy)-propane the compounds of the general Formula (X) prepared according to the Examples listed in the following Table are used as starting substances. The yields of the pure desired compound of Formula (I) calculated upon the intermediates of the general Formula (X) and the total yields in three reaction steps calculated upon the compounds of the general Formula (VIII) are also given in the following Table 1 (see also Examples 33 to 44).

EXAMPLE 25

1,2-Bis(2,2-dimethyl-5-chloropentanoyloxy)-ethane (X)

Step a)

1,2-Bis(2-methylpropanoyloxy)-ethane (IX)

A mixture of 28.0 ml (31.0 g, 0.5 mole) of ethylene glycol (VIII), 200 ml of benzene, 111.6 ml (105.8 g, 1.2 mole) of isobutyric acid and 9.5 g (0.05 mole) of p-toluenesulfonic acid monohydrate is stirred under reflux for 2.5 hours, while the water being formed is continuously separated by using a Dean-Stark apparatus. Then the mixture is cooled to about 10° C., extracted three times with 100 ml of ice-cold 1N aqueous sodium hydroxide solution, washed with water until neutral, dried over sodium sulfate and the solvent is distilled off under reduced pressure. The crude product obtained in almost quantitative yield is subjected to fractional distillation under reduced pressure. Thus 86.0 g of the desired compound are obtained in the form of a colourless oil. Yield: 85.0 %. B.p.: 74°-76° C./107 Pa. According to gas-chromatography the product is homogeneous and contains 0.3% by weight of water (determined according to Karl Fisher's method). The product thus obtained can be used directly in the next reaction step.

Step b)

1.2-Bis(2,2-dimethyl-5-chloropentanoyloxy)-ethane (X)

To a solution of 0.105 mole of lithium diisopropylamide (prepared e.g. by the method of M. T. Reetz and W. F. Maier: Annalen 1980, 1471) in 20 ml of anhydrous tetrahydrofuran 10.1 g (0.050 mole) of 1,2-bis(2-methylpropanoyloxy)-ethane prepared according to step a) above are added dropwise within about 40 minutes, under nitrogen atmosphere, keeping the temperature between 5° and 10° C. with the aid of an ice bath. Then 10 ml of anhydrous hexamethylphosphoric triamide and 12.8 ml (20.5 g, 0.13 mole) of 1-bromo-3-chloropropane are successively added dropwise and the mixture is stirred first for one hour in an ice bath, then for 19 hours without cooling. Thereafter 50 ml of water are added, the tetrahydrofuran is distilled off under reduced pressure and the residual aqueous mixture is extracted three times with 30 ml of hexane each. The hexane extracts are combined, washed three times with saturated aqueous sodium chloride solution, dried over sodium sulfate and the solvent is distilled off under reduced pressure. Thus 15.3 g of crude product are obtained in the form of a dark yellow oil. Yield: 86.1%. According to TLC on Kieselgel 60 using a 8:1 mixture of benzene and ethyl

TABLE 1

| No. of Example | No. of Example illustrating the preparation of the starting compounds of the general Formula (X) | Yields of the pure compound of Formula (I) | |
|---|---|---|---|
| | | based on the compounds of the general Formula (X) (%) | based on the compounds of the general Formula (VIII) in three reaction steps (%) |
| 13 | 33 | 39.7 | 29.9 |
| 14 | 34 | 35.8 | 28.0 |
| 15 | 35 | 57.3 | 45.1 |
| 16 | 36 | 31.1 | 27.3 |
| 17 | 37 | 53.3 | 36.8 |
| 18 | 38 | 28.6 | 18.0 |
| 19 | 39 | 26.3 | 13.6 |
| 20 | 40 | 25.9 | 16.6 |
| 21 | 41 | 63.7 | 26.1 |
| 22 | 42 | 33.1 | 11.0 |
| 23 | 43 | 26.1 | 14.6 |
| 24 | 44 | 24.2 | 16.1 | acetate $R_f=0.7$. The crude product is purified by column chromatography over 500 g of silica gel, using a 1:1 mixture of hexane and diethyl ether as eluant. Thus 12.4 g of the desired compound are obtained in the form of a pale yellow viscous oil. According to gas chromatography the product is homogeneous.

EXAMPLE 26

1,2-Bis(2,2-dimethyl-5-chloropentanoyloxy)-ethane (X)

Step a)

1,2-Bis(2-methylpropanoyloxy)-ethane (IX)

The desired compound is prepared according to step a) of Example 25.

Step b)

1,2-Bis(2,2-dimethyl-5-chloropentanoyloxy)-ethane (X)

The procedure described in step b) of Example 25 is followed except that after adding 1,2-bis(2-methylpropanoyl-oxy)-ethane hexamethylphosphoric triamide is not added to the mixture. Thus the desired compound is obtained, after purification by chromatography, in a yield of 59.2%.

EXAMPLE 27

1,3-Bis(2,2-dimethyl-5-chloropentanoyloxy)-propane (X)

Step a)

1,3-Bis(2-methylpropanoyloxy)-propane (IX)

Upon starting with a mixture of 24.4 ml (23.3 g, 0.263 mole) of isobutyric acid, 9 ml (9.5 g, 0.125 mole) of 1,3-propanediol (VIII) and 2.38 g (0.0125 mole) of p-toluenesulfonic acid monohydrate in 100 ml of benzene and proceeding according to step a) of Example 25, the desired product is obtained in crude form in a yield of 93.6%. After distillation under reduced pressure the pure desired product is obtained in a yield of 87.3%. B.p.: 92°–94° C./200 Pa.

Step b)

1,3-Bis(2,2-dimethyl-5-chloropentanoyloxy)-propane (X)

To a solution of 0.42 mole of a lithium diisopropylamide [prepared e.g. according to step b) of Example 25] in 80 ml of anhydrous tetrahydrofuran 43.2 g (0.20 mole) of 1,3-bis(2-methylpropanoyloxy)-propane prepared according to step a) above are added dropwise in an ice bath, at a temperature between about 5° C. and 10° C., under nitrogen atmosphere, within about 1 hour. Then 51.2 ml (82 g, 0.52 mole) of 1-bromo-3-chloropropane are added at the same temperature, within about 40 minutes. The mixture is stirred first in an ice bath for one hour, thereafter without cooling for further 2 hours. Then 10 ml of water are added dropwise and the tetrahydrofuran is distilled off under reduced pressure. The residue is diluted with 200 ml of water and extracted three times with 100 ml of hexane each. The organic phase is washed three times with 50 ml of water, dried over sodium sulfate and the solvent is distilled off under reduced pressure. Thus 74.0 g of the desired compound are obtained in the form of a dark yellow oil in a yield of 100%. According to TLC on Kieselgel 60 using a 8:1 mixture of benzene and ethyl acetate $R_f=0.8$. On the basis of gas chromatography the purity of the product is 77%.

EXAMPLE 28

1,3-Bis(2,2-dimethyl-5-chloropentanoyloxy)-propane (X)

Step a)

1,3-Bis(2-methylpropanoyloxy)-propane (IX)

The crude desired product is prepared according to step a) of Example 27 and used in the following reaction step without purification.

Step b)

1,3-Bis(2,2-dimethyl-5-chloropentanoyloxy)-propane (X)

The procedure described in step b) of Example 27 is followed except that crude 1,3-bis(2-methylpropanoyloxy)-propane prepared according to the above step a) is used as starting substance. Thus 18.4 g of the crude desired compound are obtained, which can be used in the following reaction step without purification. Yield (calculated upon 1,3-propanediol): 87.1%.

EXAMPLE 29

1,3-Bis(2,2-dimethyl-5-chloropentanoyloxy)-propane (X)

Step a)

1,3-Bis(2-methylpropanoyloxy)-propane (IX)

The desired compound is prepared according to step a) of Example 27.

Step b)

1,3-Bis(2,2-dimethyl-5-chloropentanoyloxy)-propane (X)

The desired compound is prepared according to step b) of Example 27, and the crude product is purified by chromatography on a silica gel column eluted with a 1:1 mixture of hexane and diethyl ether. Thus the pure desired compound is obtained in a yield of 76.3%.

EXAMPLE 30

1,3-Bis(2,2-dimethyl-5-chloropentanoyloxy)-propane (X)

Step a)

1,3-Bis(2-methylpropanoyloxy)-propane (IX)

The desired compound is prepared according to step a) of Example 27.

Step b)

1,3-Bis(2,2-dimethyl-5-chloropentanoyloxy)-propane (X)

To a mixture of 16 ml (11.2 g, 0.11 mole) of diisopropylamine and 20 ml of anhydrous tetrahydrofuran 0,76 g (0.11 mole) of lithium metal cut into pieces is added under nitrogen atmosphere. The reaction mixture is warmed to 40° C. and a solution of 8.3 g (0.065 mole) of naphtalene in 15 ml of tetrahydrofuran is added dropwise within half an hour. The mixture is stirred at 60° C. for another half an hour, cooled to a temperature between 5° C. and 10° C. and 10.8 g (0.05 mole) of 1,3-bis(2-methylpropanoyloxy)-propane prepared according to step a) above are added dropwise followed by 12.8 ml (20.5 g, 0.13 mole) of 1-bromo-3-chloropropane within 20 minutes. Then the mixture is stirred first in an ice bath for 1 hour, then at room temperature for further 2 hours and worked up according to step b) of Example 27. Thus 28.9 g of crude product are obtained in the form of a dark yellow viscous oil. According to gas-chromatography the amount of the desired compound in this oil runs to 36% by weight.

EXAMPLE 31

1,3-Bis(5-bromo-2,2-dimethylpentanoyloxy)-propane (X)

Step a)

1,3-Bis(2,2-dimethyl-4-pentenoyloxy)-propane (XIII)

To a mixture of 2.6 g (0.02 mole) of 2,2-dimethyl-4-pentenoic acid (XII) and 50 ml of hexamethylphosporic triamide a solution of 1.2 g (0.03 mole) of sodium hydroxide in 3.6 ml of water is added. The reaction mixture is stirred at room temperature for 1 hour and then 1.2 ml (2.4 g, 0.012 mole) of 1,3-dibromopropane are added. The mixture is stirred at room temperature for 4 hours, then poured onto 100 ml of 5 % aqueous hydrochloric acid and extracted twice with 50 ml of diethyl ether each. The organic phase is washed twice with 25 ml of water each, dried over sodium sulfate and the solvent is distilled off under reduced pressure. The crude product thus obtained is purified by chromatography on a silica gel column eluted with a 7:3 mixture of hexane and diethyl ether. Thus 2.03 g of the desired compound are obtained in the form of a colourless oil. Yield: 68.5%. According to TLC chromatography using the above-specified eluent $R_f=0.6$.

Step b)

1.3-Bis(5-bromo-2,2-dimethylpentanoyloxy)-propane (X)

To a solution of 6.15 g (0.02 mole) of 1,3-bis(2,2-dimethyl-4-pentenoyloxy)-propane in 20 ml of benzene 0.16 g (0.001 mole) of azo-bis(2-methylpropionitrile) are added, and 2.0 g (0.025 mole) of gaseous hydrogen bromide are introduced at room temperature, under stirring. After completion of the gas introduction the solution is stirred at room temperature for one hour. Then the solvent is removed under reduced pressure to give 9.1 g of the desired compound in crude form. Yield: 95%. According to TLC on Kieselgel 60 using a 1:1 mixture of hexane and diethyl ether $R_f=0.85$.

EXAMPLE 32

1,2-Bis(5-bromo-2,2-dimethylpentanoyloxy)-ethane (X)

Method A)

To a mixture of 2.09 g (0.01 mole) of 5-bromo-2,2-dimethylpentanoic acid (XIV), 0.31 g (0.005 mole) of ethylene glycol (VIII) and 8 ml of dichloromethane a solution of 2.07 g (0.01 mole) of dicyclohexylcarbodiimide and 0.12 g (0.001 mole) of 4-(N,N-dimethylamino)-pyridine in 8 ml of dichloromethane is added. The reaction mixture is stirred at room temperature for 24 hours. The precipitate is filtered off and the filtrate is concentrated under reduced pressure. Thus 2.0 g of the crude desired compound are obtained in a yield of 90%. According to TLC on Kieselgel 60 using a 1:1 mixture of hexane and diethyl ether $R_f=0.85$.

A sample of the crude product thus obtained is purified by chromatography on a silica gel column using a 1:1 mixture of hexane and diethyl ether as eluent. Thus the desired compound is obtained as a colourless oil, in analytically pure form. Yield: 36%.

Method B)

A mixture of 4.2 g (0.02 mole) of 5-bromo-2,2-dimethylpentanoic acid (XIV), 10 ml of benzene and 5 ml of thionyl chloride is heated under reflux for 2 hours. Then the excess of the thionyl chloride and the solvent are distilled off under reduced pressure. The residual crude 5-bromo-2,2-dimethylpentanoic chloride is dissolved in 5 ml of anhydrous benzene, and the thus-obtained solution is added dropwise to a mixture of 0.62 g (0.01 mole) of ethylene glycol (VIII), 2.8 ml (2.02 g, 0.02 mole) of triethylamine and 5 ml of anhydrous benzene at a temperature between 6° C. and 10° C. Then the reaction mixture is stirred for one hour at the same temperature and for further 6 hours at room temperature. The benzene solution is washed twice with 5 ml of ice-cold 1N sodium hydroxide solution each and three times with 5 ml of saturated aqueous sodium chloride solution each, dried over sodium sulfate and the solvent is distilled off under reduced pressure. Thus 2.89 g of the crude desired compound are obtained in a yield of 65%, which can be used in the next reaction step without purification.

EXAMPLES 33 to 44

Following the procedures described in steps a) and b) of Example 27, the multivalent alcohols of the general Formula (VIII) listed in the following Table are converted into the corresponding esters of the general Formula (IX), and then the intermediates thus obtained are converted into the corresponding halogenated multivalent esters of the general Formula (X).

The starting substances of the general Formula (VIII), the yields and boiling or melting points of the intermediates of the general Formula (IX), the yields of the crude intermediates of the general Formula (X) and the $R_f$ values determined by TLC in solvent mixtures A and B, wherein A is a 1:1 mixture of hexane and diethyl ether, and B is a 8:1 mixture of benzene and ethyl acetate, are given in the following Table 2.

TABLE 2

| No. of Example | Compound of the general Formula (VIII) | Yield and boiling point of the compound of the general Formula (IX) | | Yield and $R_f$ of the crude compound of the general Formula (X) | | |
|---|---|---|---|---|---|---|
| | | | | | $R_f$ | |
| | | (%) | °C./Pa | (%) | A | B |
| 33 | 1,2-Propanediol | 76.1 | 72–74/53.3 | 99.0 | | 0.7 |
| 34 | 1,4-Butanediol | 78.2 | 124–128/533 | 100 | 0.8 | |
| 35 | 1,6-Hexanediol | 79.7 | 144–150/400 | 98.8 | 0.8 | |
| 36 | 2-Methyl-2-(n-propyl)-1,3-propanediol | 87.9 | 118–120/67 | 100 | 0.75 | |
| 37 | Diethylene glycol | 84.1 | 122–124/106 | 82.2 | 0.6 | |
| 38 | Triethylene glycol | 67.4 | 148–152/133 | 93.5 | 0.65 | |
| 39 | glycerine | 51.7 | 130–134/267 | 100 | | 0.7 |
| 40 | Pentaerythrite | 64.4 | M.p.: 45–48° C. | 99.7 | | 0.8 |

TABLE 2-continued

| No. of Example | Compound of the general Formula (VIII) | Yield and boiling point of the compound of the general Formula (IX) | | Yield and R$_f$ of the crude compound of the general Formula (X) | | |
|---|---|---|---|---|---|---|
| | | (%) | °C./Pa | (%) | R$_f$ A | B |
| 41 | N-Phenyl-diethanolamine | 52.0[1)] | from hexane 152–160/170 | 78.8 | | 0.8 |
| 42 | N-Methyl-diethanolamine | 47.0[1)] | 114/40 | 70.4 | | 0.2 |
| 43 | Triethanolamine | 59.3[2)] | 140/106 | 94.8 | | 0.5 |
| 44 | 1,4-Bis(2-hydroxyethyl)-piperazine | 68.9[3)] | 158–164/67 | 96.3 | | 0.1 |

[1)]1.1 moles of sulfuric acid (based on the diol) are used as catalyst instead of the p-toluenesulfonic acid
[2)]Prepared by the method of Y. Arai and R. Oda (J. Chem. Soc. Japan, Ind. Eng. Sect. 57, 402 (1954); CA 1955, 4324)
[3)]Prepared according to method B) of Example 32.

EXAMPLE 45

2,2-Dimethyl-5-(2,5-dimethylphenoxy)-pentanoic acid

To a solution of 13.3 (0.0183 mole) of crude 1,3-bis(2,2-dimethyl-5-iodopentanoyloxy)-propane (purity according to gas chromatography: 76%) in 100 ml of dimethyl sulfoxide 6.0 g (0.0366 mole) of 2,5-dimethylphenyl acetate [prepared e.g. according to R. J. Highet and P. F. Highet, J. Org. Chem. 30, 902 (1965)] and 12.3 g (0.11 mole) of potassium tert-butoxide are sequentially added. The reaction mixture is stirred for 10 minutes whereafter additional 12.3 g (0.11 mole) of potassium tert-butoxide and 1.5 ml of water are added. The mixture is stirred for 1 hour and then poured into 400 ml of water. The aqueous mixture is washed three times with 80 ml portions of hexane each followed by acidification with 20% hydrochloric acid to pH=1. The acidic mixture is extracted three times with 80 ml of hexane each, these latter extracts are combined, washed three times with 80 ml of water each, dried over sodium sulfate, decolourized with 0.8 g of silica gel and concentrated under reduced pressure. In this manner 7.61 g (yield: 84.1%) of the crude desired product is obtained as a nearly colourless solid, mp. 48°–54 ° C. This crude product is recrystallized from 15 ml of acetonitrile to afford 6.32 g (yield: 70.2%) of the desired product as colourless crystals, mp. 57°–58° C. This product complies with the identity and purity requirements of the U.S. Pharmacopoeia No. XXII.

The starting 1,3-bis(2,2-dimethyl-5-iodopentanoyloxy)-propane can be prepared e.g. as follows:

A mixture of 10.0 g (0.021 mole) of crude 1,3-bis(5-chloro-2,2-dimethyl-pentanoyloxy)-propane [prepared according to step b) of Example 27, purity: 77%] and 12.5 g (0,084 mole) of sodium iodide in 100 ml of acetone is stirred under reflux for 8 hours. After cooling the precipitate is filtered off and the filtrate is concentrated under reduced pressure. The residue is dissolved in 100 ml of diethyl ether, washed three times with 40 ml of water each, dried over sodium sulfate and the solvent is evaporated under reduced pressure. In this manner 14.9 g (yield: 99%) of crude 1,3-bis(2,2-dimethyl-5-iodopentanoyloxy)-propane are obtained, purity according to gas chromatography: 76%.

EXAMPLE 46

2,2-Dimethyl-5-(2,5-dimethylphenoxy)-pentanoic acid

To a solution of 2.4 g (0.005 mole) of crude 1,3-bis(5-chloro-2,2-dimethyl-pentanoyloxy)-propane [prepared according to step b) of Example 27, purity: 77%] in 30 ml of dimethyl sulfoxide 1.64 g (0.01 mole) of 2,5-dimethylphenyl acetate, 1.5 g (0.01 mole) of sodium iodide and 3.36 g (0.03 mole) of potassium tert-butoxide are added in the above order. The mixture is stirred for 10 minutes whereafter additional 3.36 g (0.03 mole) of potassium tert-butoxide and 0.3 ml of water are added and stirring is continued for 1 hour. The product is isolated and purified as described in Example 45. In this manner the pure desired product is obtained in a yield of 41.8%.

EXAMPLE 47

By following the procedure described in Example 45, except that 2,5-dimethylphenyl isobutyrate [prepared according to the method of E. Baumgarten, J. Am. Chem. Soc. 66, 303 (1944), yield: 91%, bp. 81°–82° C./80 Pa, purity: 98,5%] is used instead of 2,5-dimethylphenyl acetate the pure title product is obtained in a yield of 63.2%.

EXAMPLE 48

By following the procedure described in Example 45, except that potassium hydroxide is used instead of potassium tert-butoxide, the pure desired product is obtained in a yield of 69.0%.

EXAMPLES 49–53

By following the procedure described in Example 45 and starting with the compounds of the general Formula (X) wherein X is iodo and Z is as given in the Table 3 below, the final product of Formula (I) is obtained with the yields given in the Table. The starting iodo compounds are prepared as given for the starting compound of Example 45 above, starting with the chloro analogues prepared as described above. The Rf values of the starting iodo compounds are given in the Table, too.

TABLE 3

| Example No. | Z | Yield of (I) (%) | Rf of the starting iodo compound* |
|---|---|---|---|
| 49 | 1,6-Hexylene | 65.8 | 0.70 |
| 50 | 3-Oxa-1,5-pentylene | 64.3 | 0.65 |
| 51 | 3-(N-Phenylaza)-1,5-pentylene | 51.2 | 0.75 |
| 52 | 3-(N-Methylaza)-1,5-pentylene | 54.2 | 0.70 |
| 53 | 2-(2,2-Dimethyl-5-iodopentanoyloxy)-1,3-propylene | 42.1 | 0.70 |

*Adsorbent: Kieselgel 60, solvent system: 8:1 mixture of benzene and ethyl acetate

What we claim is:
1. A compound of the general formula

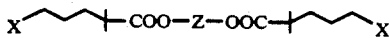

wherein
- X represents halogen and
- Z stands for a straight or branched chain $C_{1-8}$ alkylene group optionally substituted by one or two 2,2-dimethyl-5-halopentanoyloxy group(s), wherein halo represents chlorine or bromine, and in which alkylene group one or two methylene group(s) may be optionally replaced either by hetero atom(s) or by a bivalent heterocyclic group.

2. The compound as defined in claim 1 wherein said hetero atom(s) is oxygen and/or nitrogen atom(s), which latter may be optionally substituted by phenyl or $C_{1-4}$ alkyl optionally substituted by a 2,2-dimethyl-5-halopentanoyloxy group.

3. The compound as defined in claim 1 wherein said heterocyclic group is a piperazine-1,4-diyl group.

4. The compound as defined in claim 2 wherein said heterocyclic group is a piperazine-1,4-diyl group.

5. 1,3-Bis(2,2-dimethyl-5-chloropentanoyloxy)-propane.

6. 1,3-Bis(2,2-dimethyl-5-iodopentanoyloxy)-propane.

7. 1,6-Bis(2,2-dimethyl-5-chloropentanoyloxy)-hexane.

8. Bis[2-(2,2-dimethyl-5-chloropentanoyloxy)-ethyl]-ether.

* * * * *